(12) United States Patent
Casado Zapico et al.

(10) Patent No.: US 11,312,989 B1
(45) Date of Patent: Apr. 26, 2022

(54) MATERIALS AND METHODS FOR AGE-AT-DEATH ESTIMATION

(71) Applicants: Sara Casado Zapico, Miami Beach, FL (US); Bruce R. McCord, Miami, FL (US)

(72) Inventors: Sara Casado Zapico, Miami Beach, FL (US); Bruce R. McCord, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/207,638

(22) Filed: Mar. 20, 2021

(51) Int. Cl.
| C12Q 1/6876 | (2018.01) |
| C12Q 1/6858 | (2018.01) |
| C12Q 1/6806 | (2018.01) |
| C12Q 1/68   | (2018.01) |
| C07H 21/00  | (2006.01) |

(52) U.S. Cl.
CPC ......... *C12Q 1/6858* (2013.01); *C12Q 1/6806* (2013.01); *C12Q 1/6876* (2013.01)

(58) Field of Classification Search
CPC ......... C12Q 1/68; C12Q 1/6876; C07H 21/00
See application file for complete search history.

(56) References Cited

U.S. PATENT DOCUMENTS

| 10,087,486 B2 * | 10/2018 | Zhang ............... C12Q 1/6881 |
| 10,344,323 B1 * | 7/2019 | McCord ............... C12Q 1/686 |
| 2003/0181406 A1 * | 9/2003 | Schetter ............... C07H 21/00 514/44 R |
| 2006/0019270 A1 * | 1/2006 | Yang ............... C12Q 2523/125 435/6.12 |
| 2015/0259742 A1 * | 9/2015 | Zhang ............... C12Q 1/6883 506/9 |
| 2020/0407802 A1 * | 12/2020 | Berman ............... C12Q 1/6883 |

FOREIGN PATENT DOCUMENTS

| CN | 110257494 A | * | 9/2019 |
| WO | WO 2012/162139 | * | 11/2012 |

OTHER PUBLICATIONS

Ahern, H. The Scientist 9(15) : 20 (Year: 1995).*
Garcia et al., Effect of environmental factors on PCR-DNA analysis from dental pulp. Intl. J. of Legal Med.109:125-129 (Year: 1996).*
Giuilani et al. Inferring Chronological Age from DNA Methylation Patterns of Human Teeth. Am. J of Physical Anthropology 159 :585-595 (Year: 2016).*
Jabbari et al., Cytosine methylation and CpG, TpG (CpA) and TpAfrequencies. Gene 333 :143-149 (Year: 2004).*
Mayne et al., A DNA methylation age predictor for zebrafish. Aging 12(24) : 24817 (Year: 2020).*
Potsch et al., Application of DNA techniques for identification using human dental pulp as a source of DNA. Intl. J. of Legal Med. 105:139-143 (Year: 1992).*
Simmen, MW., Genome-scale relationships between cytosine methylation and dinucleotide abundances in animals. Genomics 92 : 33-40 (Year: 2008).*
Zhao et all.Methylation-Dependent Transition Rates Are Dependent on Local Sequence Lengths and Genomic Regions.Mol. Biol. Evol. 24(1) :23-25 (Year: 2006).*
Yi et al., Forensic Science International :Genetics 11 :117-125 (Year: 2014).*
English Machine translation of Huang et al. CN 110257494—Dialog For. Patent Finder (Sep. 2019) (Year: 2019).*
Alghanim, H., et al., "Detection and evaluation of DNA methylation markers found at SCGN and KLF14 loci to estimate human age." Forensic Science International: Genetics, 2017, 31: 81-88.
Bekaert, B., et al., "Improved age determination of blood and teeth samples using a selected set of DNA methylation markers." Epigenetics, Oct. 2015, 10(10): 922-930.
Correia Dias, H., et al., "DNA methylation age estimation from human bone and teeth." Australian Journal of Forensic Sciences, 2021, pp. 1-14.
Giuliani, C., et al., "Inferring Chronological Age from DNA Methylation Patterns of Human Teeth." American Journal of Physical Anthropology, 2016, 159: 585-595.
Marquez-Ruiz, A.B., et al., "DNA methylation levels and telomere length in human teeth: usefulness for age estimation." International Journal of Legal Medicine, 2020, 134: 451-459.
Santos Silva, D.S.B., et al., "Evaluation of DNA methylation markers and their potential to predict human aging." Electrophoresis, 2015, 36(15): 1775-1780.

* cited by examiner

*Primary Examiner* — Ethan C Whisenant
(74) *Attorney, Agent, or Firm* — Saliwanchik, Lloyd & Eisenschenk

(57) ABSTRACT

Provided are materials and methods for age-at-death estimation for identification of human remains in forensic contexts. In preferred embodiments, the methods and materials comprise methylation analysis of human tooth pulp tissue and selected genes wherein the methylation analysis of selected CpG dinucleotides within the selected genes provides a surprising accuracy of age determination from small amount of tooth pulp DNA.

20 Claims, 1 Drawing Sheet
Specification includes a Sequence Listing.

SEQUENCE LISTING

```
<160> NUMBER OF SEQ ID NOS: 20

<210> SEQ ID NO 1
<211> LENGTH: 21
<212> TYPE: DNA
<213> ORGANISM: Artificial sequence
<220> FEATURE:
<223> OTHER INFORMATION: primer

<400> SEQUENCE: 1
aggggagtag ggtaagtgag g                                      21

<210> SEQ ID NO 2
<211> LENGTH: 24
<212> TYPE: DNA
<213> ORGANISM: Artificial sequence
<220> FEATURE:
<223> OTHER INFORMATION: primer

<400> SEQUENCE: 2
aacaaaacca tttcccccta atat                                   24

<210> SEQ ID NO 3
<211> LENGTH: 25
<212> TYPE: DNA
<213> ORGANISM: Artificial sequence
<220> FEATURE:
<223> OTHER INFORMATION: primer

<400> SEQUENCE: 3
acaaccaata aatattccta aaact                                  25
```

```
<210> SEQ ID NO 4
<211> LENGTH: 32
<212> TYPE: DNA
<213> ORGANISM: Homo sapiens

<400> SEQUENCE: 4
ccrtaaacrt taaaccrccr crcraaaccr ac                                       32

<210> SEQ ID NO 5
<211> LENGTH: 23
<212> TYPE: DNA
<213> ORGANISM: Artificial sequence
<220> FEATURE:
<223> OTHER INFORMATION: primer

<400> SEQUENCE: 5
ggttgtgaga aggtaggaga ttt                                                 23

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6
accaacaacc ccaacatccc                                                     20

<210> SEQ ID NO 7
<211> LENGTH: 21
<212> TYPE: DNA
<213> ORGANISM: Artificial sequence
<220> FEATURE:
<223> OTHER INFORMATION: primer

<400> SEQUENCE: 7
agaaggtagg agattttgt t                                                    21

<210> SEQ ID NO 8
<211> LENGTH: 76
<212> TYPE: DNA
<213> ORGANISM: Homo sapiens

<400> SEQUENCE: 8
tygyggtgta ygygattty gagaygatag ygyggttatt gttagtagyg aaggygtttt          60
tygyggagyg tttyga                                                         76

<210> SEQ ID NO 9
<211> LENGTH: 25
<212> TYPE: DNA
<213> ORGANISM: Artificial sequence
<220> FEATURE:
<223> OTHER INFORMATION: primer

<400> SEQUENCE: 9
tgtttttagg gttttgggag tatag                                               25

<210> SEQ ID NO 10
<211> LENGTH: 27
<212> TYPE: DNA
<213> ORGANISM: Artificial sequence
<220> FEATURE:
<223> OTHER INFORMATION: primer

<400> SEQUENCE: 10
```

```
acacctccta aaacttctcc aatctcc                                        27
```

<210> SEQ ID NO 11
<211> LENGTH: 17
<212> TYPE: DNA
<213> ORGANISM: Artificial sequence
<220> FEATURE:
<223> OTHER INFORMATION: primer

<400> SEQUENCE: 11

```
ggttttggga gtatagt                                                   17
```

<210> SEQ ID NO 12
<211> LENGTH: 48
<212> TYPE: DNA
<213> ORGANISM: Homo sapiens

<400> SEQUENCE: 12

```
agttatyggg agygtygttt tyggygtggg tttttgggyg agtttygg                 48
```

<210> SEQ ID NO 13
<211> LENGTH: 26
<212> TYPE: DNA
<213> ORGANISM: Artificial sequence
<220> FEATURE:
<223> OTHER INFORMATION: primer

<400> SEQUENCE: 13

```
tttggtgtag ttagggaagg ggtatt                                         26
```

<210> SEQ ID NO 14
<211> LENGTH: 27
<212> TYPE: DNA
<213> ORGANISM: Artificial sequence
<220> FEATURE:
<223> OTHER INFORMATION: primer

<400> SEQUENCE: 14

```
caccaacaac ctctaataaa ttctcta                                        27
```

<210> SEQ ID NO 15
<211> LENGTH: 15
<212> TYPE: DNA
<213> ORGANISM: Artificial sequence
<220> FEATURE:
<223> OTHER INFORMATION: primer

<400> SEQUENCE: 15

```
gggaagggt attgg                                                      15
```

<210> SEQ ID NO 16
<211> LENGTH: 85
<212> TYPE: DNA
<213> ORGANISM: Homo sapiens

<400> SEQUENCE: 16

```
tggygtttgg tagtaggtgt gatagattt tttygggyg tttgattygy ggyggggyg       60 gggtttgttt ttagggtttt tttag                                          85
```

<210> SEQ ID NO 17
<211> LENGTH: 27
<212> TYPE: DNA
<213> ORGANISM: Artificial sequence
<220> FEATURE:

```
<223> OTHER INFORMATION: primer

<400> SEQUENCE: 17
aaggagtttt ttttaaagtt gtttagg                                          27

<210> SEQ ID NO 18
<211> LENGTH: 28
<212> TYPE: DNA
<213> ORGANISM: Artificial sequence
<220> FEATURE:
<223> OTHER INFORMATION: primer

<400> SEQUENCE: 18
acaacccaaa tccataactt ttcctaca                                         28

<210> SEQ ID NO 19
<211> LENGTH: 24
<212> TYPE: DNA
<213> ORGANISM: Artificial sequence
<220> FEATURE:
<223> OTHER INFORMATION: primer

<400> SEQUENCE: 19 ttttttaaa gttgtttagg tttt                                              24

<210> SEQ ID NO 20
<211> LENGTH: 91
<212> TYPE: DNA
<213> ORGANISM: Homo sapiens

<400> SEQUENCE: 20
ttygygtygg tgtttggttt tygtygttaa tattatggat agttttyggg aatygatttt      60
ggggygtttg gaygtygttg gtttttggta g                                     91
```

US 11,312,989 B1

MATERIALS AND METHODS FOR AGE-AT-DEATH ESTIMATION

GOVERNMENT SUPPORT

This invention was made with government support under IIP1739805 awarded by National Science Foundation (CARFS). The government has certain rights in the invention.

SEQUENCE LISTING

The Sequence Listing for this application is labeled "SeqList-103ct21_ST20", which was created on Feb. 3, 2021, and is 4 KB. The entire content is incorporated herein by reference in its entirety.

BACKGROUND OF THE INVENTION

In forensic cases involving skeletal remains, the creation of a biological profile by a forensic anthropologist is essential to compare with missing persons reports, to sort out the number of possible matches and to identify the victim. Biological profiles commonly include sex, age, ancestry, and height. Thus, age estimation is one of the key analyses in the identification of the remains. Although age can be assessed very accurately in childhood because forensic anthropological age assessment is based on growth and developmental markers, this estimation is less accurate in adults, where the assessment is typically based on degenerative changes of bones and teeth.

The application of biochemical techniques, based on the natural process of aging, may provide a potential solution to this problem. For example, until recently, the racemization of aspartic acid in dentin seemed to be the most accurate technique to determine the age in adult individuals.

However, epigenetics, the study of heritable changes in gene function that do not change the DNA sequence, has emerged as a valuable and more accurate tool for age estimation because epigenetic modifications can generally be associated with chronological age. An epigenetic drift is associated with age. Global DNA methylation levels decrease during aging although specific local CpG sites can either become hypo- or hypermethylated with aging.

The CpG dinucleotide distribution is uneven, with several short DNA elements having a much higher density of CpG dinucleotides than other regions of the genome, forming the so-called CpG islands. Most of these islands are located near transcription start sites. Previous studies looked at specific regions of the genome and observed that specific genome locations can either increase or decrease the methylation level with age, most likely due to differences in gene expression in each cell type. CpG sites that become hypermethylated with aging are primarily located in CpG islands, whereas the hypomethylated CpGs are generally located outside of CpG islands.

To determine the pattern of DNA methylation at a locus, the most commonly used methods include the bisulfite modification of genomic DNA, which chemically converts the unmethylated cytosines to uracils but does not react with methylated cytosines. During subsequent polymerase chain reaction (PCR), the uracils get copied as thymines and the amplicons can then be sequenced to determine the presence of a cytosine or a thymine at each specific CpG.

Teeth, as the hardest structures in the human body, can survive after everything else has decomposed. Particularly, dental pulp is protected from external forces by hard tissues. Pulp is located in the central region of the tooth and is formed by a stromal tissue containing nerves, blood, and lymphatic vessels.

Because age-at-death estimation constitutes one of the key parameters for identification of human remains in forensic contexts and current age estimation techniques in adult individuals lead to estimates that are only accurate to within ±10 years of chronological age, more accurate and reliable age estimation methods are needed.

BRIEF SUMMARY OF THE INVENTION

The subject invention provides materials and methods for age determination of a subject using tooth pulp tissue and improved DNA methylation determination techniques.

In some embodiments, the methods of the invention comprise amplifying bisulfite treated genomic DNA from tooth pulp to quantify DNA methylation in at least one DNA amplicon for age determination, where the at least one DNA amplicon, according to the invention, can be an amplicon from an ELOVL2, NPTX2, FHL2, KLF14, and/or an SCGN gene.

The methods further provide models for predicting an age of a subject from quantified CpG dinucleotides present in a bisulfite treated DNA of a DNA amplicon. In specific embodiments, the models utilize multi-variant analysis and enable highly accurate age prediction due to the specific methylation analysis employed.

Advantageously, the methods and models of the invention not only allow an age determination based on a small number of CpG dinucleotides but can also enable a surprising age determination accuracy of between 1.2 years and 2.5 years.

Further provided are methods for preparing a DNA sample for age determination of a subject, wherein the DNA sample comprises amplicons of an ELOVL2, NPTX2, FHL2, KLF14, and/or an SCGN gene and is used for high accuracy age determination.

BRIEF DESCRIPTION OF THE SEQUENCES

Figure 1A:
FIG. 1A shows the predicted versus chronological age determining by model 1.

SEQ ID NO:1: Forward primer for ELOVL2.
SEQ ID NO:2: Reverse primer for ELOVL2.
SEQ ID NO:3: Sequencing primer for ELOVL2.
SEQ ID NO:4: Nucleotide sequence of region of interest in the ELOVL2 gene.
SEQ ID NO:5: Forward primer for NPTX2.
SEQ ID NO:6: Reverse primer for NPTX2.
SEQ ID NO:7: Sequencing primer for NPTX2.
SEQ ID NO:8: Nucleotide sequence of region of interest in the NPTX2 gene.
SEQ ID NO:9: Forward primer for FHL2.
SEQ ID NO:10: Reverse primer for FHL2.
SEQ ID NO:11: Sequencing primer for FHL2.
SEQ ID NO:12: Nucleotide sequence of region of interest in the FHL2 gene.
SEQ ID NO:13: Forward primer for KLF14.
SEQ ID NO:14: Reverse primer for KLF14.

SEQ ID NO:15: Sequencing primer for KLF14.
SEQ ID NO:16: Nucleotide sequence of region of interest in the KLF14 gene.
SEQ ID NO:17: Forward primer for SCGN.
SEQ ID NO:18: Reverse primer for SCGN.
SEQ ID NO:19: Sequencing primer for SCGN.
SEQ ID NO:20: Nucleotide sequence of region of interest in the SCGN gene.

DETAILED DESCRIPTION OF THE INVENTION

The subject invention provides materials and methods for age determination of a subject using tooth pulp tissue and improved DNA methylation determination techniques.

Because teeth are the hardest structures in the human body and can survive after other structures have decomposed, the methods and materials of the invention for age determination of human remains preferentially employ tooth pulp tissue.

Tooth pulp is located in the central region of the tooth, is formed by a stromal tissue containing nerves, blood, and lymphatic vessels, and is protected from external forces by hard tissues, making it a suitable tissue for DNA analysis; however, all biological samples can be used according to the methods of the invention, as long as the biological samples contain cells or DNA of cells.

In some embodiments, DNA is isolated from a tissue sample and bisulfite treated. In preferred embodiments, the tissue sample is tooth pulp and the DNA isolated from the tooth pulp is bisulfite treated and analyzed using quantitative DNA methylation analysis methods. In some embodiments, the quantitative DNA methylation analysis is performed using an assay selected from, for example, Sanger sequencing, pyrosequencing, SNaPshot and MALDI-TOF spectrometry.

In preferred embodiments, the DNA isolated from tooth pulp is bisulfite treated and quantitative DNA methylation analysis is performed using pyrosequencing.

In some embodiments, at least one region of interest within the bisulfite treated DNA is amplified by PCR for quantitative methylation analysis and age determination. In some embodiments, from at least one to about 50 regions of interest within the bisulfite treated DNA are amplified; or about 2 to about 40; about 3 to about 30; about 4 to about 20; or about 5 to about 10 regions of interest within the bisulfite treated DNA are amplified. Specifically, the regions of interest of the instant invention originate from specific genes identified by methods of the invention to comprise CpG dinucleotides that are differentially methylated at different ages of an individual.

In some embodiments, the methods of the invention analyze DNA methylation levels of at least 1, 2, 3, 4, 5, 6, 7, 8, 9 and/or 10 specific genes. In preferred embodiments, the methods and models of the invention analyze DNA methylation levels of at least two genes. In further preferred embodiments, the methods of the invention analyze DNA methylation levels of at least four genes. In yet further preferred embodiments, the methods of the invention analyze DNA methylation levels of five genes.

In specific embodiments, the at least one gene to be analyzed by the methods of the invention is selected from an ELOVL2, KLF14, SCGN, NPTX2, and/or FHL2 gene.

ELOVL2 encodes a transmembrane protein involved in the synthesis of long ω3 and ω6 polyunsaturated fatty acids (PUFA).

FHL2 is a transcriptional co-factor that acts as a scaffolding protein in signaling processes, including: cell cycle regulation, differentiation, assembly of extracellular matrix, bone formation, and wound healing.

The gene KLF14 on chromosome 7 is a member of the Krüppel-like factor family of transcription factors that regulate the transcription of various genes. KLF14 appears to be a master regulator of gene expression in adipose tissue.

The gene SCGN on chromosome 6 encodes a secretagogin protein, a secreted calcium-binding protein found in the cytoplasm, which is involved in potassium chloride stimulated calcium flux as well as cell proliferation. Surprisingly, SCGN plays a key role in age estimation, as both CpGs 3 and 8 produced among the highest correlations in the genes analyzed (except ELOVL2 CpG1 and CpG7).

NPTX2 (neuronal pentraxin II) is involved in synapse formation.

In some embodiments, the methods of the invention comprise an analysis of genes comprising at least two genes of; at least three genes of; or at least four genes of ELOVL2, KLF14, SCGN, NPTX2, and FHL2 genes.

In some embodiments, the methods of the invention comprise an analysis of all of ELOVL2, KLF14, SCGN, NPTX2, and FHL2 genes.

In some embodiments, the methods of the invention comprise an analysis of at least an ELOVL2 gene and at least one further gene selected from a KLF14, SCGN, NPTX2, and FHL2 gene.

In some embodiments, if an ELOVL2 gene is analyzed by the methods of the invention, at least one other gene from the group of SCGN, KLF14, NPTX2, and FHL2 genes is also analyzed.

In some embodiments, the methods of the invention comprise an analysis of at least an ELOVL2 gene and at least an FHL2 gene.

In some embodiments, the methods of the invention comprise an analysis of at least an SCGN gene and at least one further gene selected from a KLF14, ELOVL2, NPTX2, and FHL2 gene.

In some embodiments, if a NPTX2 gene is analyzed by the methods of the invention, at least one other gene from the group of SCGN, KLF14, ELOVL2, and FHL2 genes is also analyzed.

In preferred embodiments, specific amplicons of an ELOVL2, SCGN, KLF14, NPTX2, and/or FHL2 gene are analyzed according to the subject invention.

In some embodiments, the amplicon of an ELOV2 gene comprises SEQ ID NO: 4.

In some embodiments, the amplicon of a NPTX2 gene comprises SEQ ID NO: 8.

In some embodiments, the amplicon of FHL2 gene comprises SEQ ID NO: 12.

In some embodiments, the amplicon of a KLF14 gene comprises SEQ ID NO: 16.

In some embodiments, the amplicon of an SCGN gene comprises SEQ ID NO: 20.

In further embodiments, the amplicons of an ELOVL2, KLF14, SCGN, NPTX2, and/or FHL2 gene are generated from bisulfite treated DNA of a subject. In preferred embodiments, the amplicons of an ELOVL2, KLF14, SCGN, NPTX2, and/or FHL2 gene are generated from bisulfite treated tooth pulp DNA.

In preferred embodiments, the amplicons of an ELOVL2 gene are generated from bisulfite treated DNA using primers of SEQ ID NOs: 1 and 2.

In further preferred embodiments, the amplicons of an NPTX2 gene are generated from bisulfite treated DNA using primers of SEQ ID NOs: 5 and 6.

In yet further preferred embodiments, the amplicons of an FHL2 gene are generated from bisulfite treated DNA using primers of SEQ ID NOs: 9 and 10.

In yet further preferred embodiments, the amplicons of a KLF14 gene are generated from bisulfite treated DNA using primers of SEQ ID NOs: 13 and 14.

In yet further preferred embodiments, the amplicons of an SCGN gene are generated from bisulfite treated DNA using primers of SEQ ID NOs: 17 and 18.

In some embodiments, the methods of the invention measure DNA methylation levels of about 1 to about 50 CpGs in an amplicon generated from an ELOVL2, KLF14, SCGN, NPTX2, and/or FHL2 gene. For example, methylation levels at about 2 to about 48 CpGs; about 3 to about 46 CpGs; about 4 to about 44 CpGs; about 5 to about 42 CpGs; about 6 to about 40 CpGs; about 7 to about 38 CpGs; about 8 to about 36 CpGs; about 9 to about 34 CpGs; about 10 to about 32 CpGs; about 111 to about 30 CpGs; about 12 to about 28 CpGs; about 13 to about 26 CpGs; about 14 to about 24 CpGs; about 15 to about 22 CpGs; or about 16 to about 20 CpGs are quantified.

Also provided are age prediction models that provide advantageous age estimation accuracies with a low number of input variables.

In some embodiments, the methods using the age prediction models of the invention predict the age of a subject with a mean absolute error of below 2.5 years.

In some embodiments, the methods using the age prediction models of the invention predict the age of a subject with a mean absolute error of below 2 years; or below 1.9 years; 1.8 years; 1 years; about 2.3 years to about 1.2 years; of about 2.2 years to about 1.3 year; about 2.1 year to about 1.4 years; about 2 years to about 1.5 years; of about 1.9 years to about 1.6 year; about 1.8 year to about 1.7 years; or about 1.2 years; about 1.3 years; about 1.4 years; about 1.5 years; about 1.6 years; about 1.7 years; about 1.8 years; about 1.9 years; about 2 years; about 2.1 years; about 2.2 years; about 2.3 years; about 2.4 or about 2.5 years.

In some embodiments, the methods of the invention amplify bisulfite treated DNA of any of an ELOVL2, KLF14, SCGN, NPTX2, and/or FHL2 gene using singleplex PCR. In some embodiments, the methods of the invention further utilize multivariant regression models and leave-one-out cross validation models. In some embodiments, the methods of the invention amplify bisulfite treated DNA of at least two of an ELOVL2, KLF14, SCGN, NPTX2, and/or FHL2 gene using multiplex PCR.

In specific embodiments, specific CpG positions within an amplicon generated from an ELOVL2, KLF14, SCGN, NPTX2, and/or FHL2 gene are selected, methylation levels are quantified at the selected CpG positions and the age at death of the subject from whom the DNA originated is calculated.

In some embodiments, the amplicon comprises SEQ ID NO: 4, which comprises 7 CpG positions, and the CpG position selected for age determination is any one of CpG1 to CpG7 of SEQ ID NO: 4. In some embodiment, the CpG positions selected for age determination are two or more of CpG1 to CpG7 of SEQ ID NO: 4. In some embodiments, the CpG positions selected for age determination are all of CpG1 to CpG7 of SEQ ID NO: 4. In preferred embodiments, the CpG positions selected for age determination are CpG1, CpG2, CpG3, CpG5, CpG6, and CpG7 of SEQ ID NO: 4.

In some embodiments, the amplicon comprises SEQ ID NO: 8, which comprises 14 CpG positions, and the CpG position selected for age determination is any one of CpG1 to CpG14 of SEQ ID NO: 8. In some embodiments, the CpG positions selected for age determination are two or more of CpG1 to CpG14 of SEQ ID NO: 8. In some embodiments, the CpG positions selected for age determination are all of CpG1 to CpG14 of SEQ ID NO: 8. In preferred embodiments, the CpG position selected for age determination is CpG4 of SEQ ID NO: 8.

In some embodiments, the amplicon comprises SEQ ID NO: 12, which comprises 8 CpG positions, and the CpG position selected for age determination is any one of CpG1 to CpG8 of SEQ ID NO: 12. In some embodiments, the CpG positions selected for age determination are two or more of CpG1 to CpG8 of SEQ ID NO: 12. In some embodiments, the CpG positions selected for age determination are all of CpG1 to CpG8 of SEQ ID NO: 12. In preferred embodiments, the CpG positions selected for age determination from SEQ ID NO: 12 are selected together with at least one CpG position of at least one of a SEQ ID NOs: 4, 8, 16, and/or for methylation quantification and age determination using the methods of the invention.

In some embodiments, the amplicon comprises SEQ ID NO: 16, which comprises 7 CpG positions, and the CpG position selected for age determination is any one of CpG1 to CpG7 of SEQ ID NO: 16. In some embodiments, the CpG positions selected for age determination are two or more of CpG1 to CpG7 of SEQ ID NO: 16. In some embodiments, the CpG positions selected for age determination are all of CpG1 to CpG7 of SEQ ID NO: 16. In preferred embodiments, the CpG position selected for age determination is CpG7 of SEQ ID NO: 16.

In some embodiments, the amplicon comprises SEQ ID NO: 20, which comprises 10 CpG positions, and the CpG position selected for age determination is any one of CpG1 to CpG10 of SEQ ID NO: 20. In some embodiments, the CpG positions selected for age determination are two or more of CpG1 to CpG10 of SEQ ID NO: 20. In some embodiments, the CpG positions selected for age determination are all of CpG1 to CpG10 of SEQ ID NO: 20. In preferred embodiments, the CpG position selected for age determination is any of CpG3 and/or CpG8 of SEQ ID NO: 20.

In some embodiments, the methods of the invention comprise a quantification of DNA methylation levels at about 10 to about 15 CpG positions selected from SEQ ID NOs: 4, 8, 12, 16, and 20.

In preferred embodiments, the methods of the invention comprise the quantification of DNA methylation levels at 14, 13, 12, or 11 CpG positions selected from SEQ ID NOs: 4, 8, 12, 16, and 20.

In some embodiments, the methods of the invention comprise a quantification of DNA methylation levels of at least CpG positions CpG2, CpG3, CpG4, CpG5, and CpG7 of SEQ ID NO: 4.

In some embodiments, the methods of the invention comprise a quantification of DNA methylation levels of at least CpG positions CpG2, CpG3, CpG4, and CpG7 of SEQ ID NO: 4.

In further embodiments, the methods of the invention comprise a quantification of DNA methylation levels of at least CpG position CpG4 of SEQ ID NO: 8.

In some embodiments, the methods of the invention comprise a quantification of DNA methylation levels of at least CpG positions CpG1, CpG3, CpG4, CpG5, and CpG6 of SEQ ID NO: 12.

In some embodiments, the methods of the invention comprise a quantification of DNA methylation levels of at least CpG positions CpG1, CpG3, CpG4, and CpG5 of SEQ ID NO: 12.

In some embodiments, the methods of the invention comprise a quantification of DNA methylation levels of at least CpG position CpG7 of SEQ ID NO: 16. In other embodiments, the methods of the invention comprise a quantification of DNA methylation levels of CpG positions of SEQ ID NOs: 4, 8, 12, and 20 without quantification of any CpG positions of SEQ ID NO: 16.

In some embodiments, the methods of the invention comprise a quantification of DNA methylation levels of at least CpG positions CpG2, CpG3, CpG4, CpG5, and CpG7 of SEQ ID NO: 4 and at least CpG position CpG4 of SEQ ID NO: 8.

In some embodiments, the methods of the invention comprise a quantification of DNA methylation levels of at least CpG positions CpG2, CpG3, CpG4, CpG5, and CpG7 of SEQ ID NO: 4 and at least CpG positions CpG1, CpG3, CpG4, CpG5, and CpG6 of SEQ ID NO: 12.

In some embodiments, the methods of the invention comprise a quantification of DNA methylation levels of at least CpG positions CpG2, CpG3, CpG4, CpG5, and CpG7 of SEQ ID NO: 4 and at least CpG positions CpG1, CpG3, CpG4, and CpG5 of SEQ ID NO: 12.

In some embodiments, the methods of the invention comprise a quantification of DNA methylation levels of at least CpG positions CpG2, CpG3, CpG4, CpG5, and CpG7 of SEQ ID NO: 4 and at least CpG position CpG7 of SEQ ID NO: 16.

In some embodiments, the methods of the invention comprise a quantification of DNA methylation levels of at least CpG positions CpG2, CpG3, CpG4, CpG5, and CpG7 of SEQ ID NO: 4 and at least CpG position CpG3 and CpG8 of SEQ ID NO: 20.

In some embodiments, the methods of the invention comprise a quantification of DNA methylation levels of at least CpG4 position of SEQ ID NO: 8 and at least CpG positions CpG1, CpG3, CpG4, CpG5, and CpG6 of SEQ ID NO: 12.

In some embodiments, the methods of the invention comprise a quantification of DNA methylation levels of at least CpG4 position of SEQ ID NO: 8 and at least CpG positions CpG1, CpG3, CpG4, and CpG5 of SEQ ID NO: 12.

In some embodiments, the methods of the invention comprise a quantification of DNA methylation levels of at least CpG4 position of SEQ ID NO: 8 and at least CpG position CpG7 of SEQ ID NO: 16.

In some embodiments, the methods of the invention comprise a quantification of DNA methylation levels of at least CpG4 position of SEQ ID NO: 8 and at least CpG positions CpG3 and CpG8 of SEQ ID NO: 20.

In some embodiments, the methods of the invention comprise a quantification of DNA methylation levels of at least CpG positions CpG1, CpG3, CpG4, CpG5, and CpG6 of SEQ ID NO: 12 and at least CpG position CpG7 of SEQ ID NO: 16.

In some embodiments, the methods of the invention comprise a quantification of DNA methylation levels of at least CpG positions CpG1, CpG3, CpG4, CpG5, and CpG6 of SEQ ID NO: 12 and at least CpG position CpG3 and CpG8 of SEQ ID NO: 20.

In some embodiments, the methods of the invention comprise a quantification of DNA methylation levels of at least CpG position CpG7 of SEQ ID NO: 16 and at least CpG position CpG3 and CpG8 of SEQ ID NO: 20.

In some embodiments, the methods of the invention comprise a quantification of DNA methylation levels of at least CpG positions CpG2, CpG3, CpG4, CpG5, and CpG7 of SEQ ID NO: 4, at least CpG position CpG4 of SEQ ID NO: 8, and at least CpG positions CpG1, CpG3, CpG4, CpG5, and CpG6 of SEQ ID NO: 12.

In some embodiments, the methods of the invention comprise a quantification of DNA methylation levels of at least CpG positions CpG2, CpG3, CpG4, CpG5, and CpG7 of SEQ ID NO: 4, at least CpG position CpG4 of SEQ ID NO: 8, and at least CpG positions CpG1, CpG3, CpG4, and CpG5 of SEQ ID NO: 12.

In some embodiments, the methods of the invention comprise a quantification of DNA methylation levels of at least CpG positions CpG2, CpG3, CpG4, CpG5, and CpG7 of SEQ ID NO: 4, at least CpG position CpG4 of SEQ ID NO: 8, and at least CpG position CpG7 of SEQ ID NO: 16.

In some embodiments, the methods of the invention comprise a quantification of DNA methylation levels of at least CpG positions CpG2, CpG3, CpG4, CpG5, and CpG7 of SEQ ID NO: 4, at least CpG position CpG4 of SEQ ID NO: 8, and at least CpG position CpG3 and CpG8 of SEQ ID NO: 20.

In some embodiments, the methods of the invention comprise a quantification of DNA methylation levels of at least CpG4 position of SEQ ID NO: 8 and at least CpG positions CpG1, CpG3, CpG4, CpG5, and CpG6 of SEQ ID NO: 12, and at least CpG7 of SEQ ID NO: 16.

In some embodiments, the methods of the invention comprise a quantification of DNA methylation levels of at least CpG4 position of SEQ ID NO: 8 and at least CpG positions CpG1, CpG3, CpG4, CpG5, and CpG6 of SEQ ID NO: 12, and at least CpG3 and CpG8 of SEQ ID NO: 20.

In some embodiments, the methods of the invention comprise a quantification of DNA methylation levels of at least CpG4 position of SEQ ID NO: 8 and at least CpG positions CpG1, CpG3, CpG4, and CpG5 of SEQ ID NO: 12, and at least CpG3 and CpG8 of SEQ ID NO: 20.

In some embodiments, the methods of the invention comprise a quantification of DNA methylation levels of at least CpG positions CpG2, CpG3, CpG4, CpG5, and CpG7 of SEQ ID NO: 4, at least CpG positions CpG1, CpG3, CpG4, CpG5, and CpG6 of SEQ ID NO: 12, and at least CpG position CpG7 of SEQ ID NO: 16.

In some embodiments, the methods of the invention comprise a quantification of DNA methylation levels of at least CpG positions CpG2, CpG3, CpG4, CpG5, and CpG7 of SEQ ID NO: 4, at least CpG positions CpG1, CpG3, CpG4, CpG5, and CpG6 of SEQ ID NO: 12, and at least CpG position CpG3 and CpG8 of SEQ ID NO: 20.

In some embodiments, the methods of the invention comprise a quantification of DNA methylation levels of at least CpG positions CpG2, CpG3, CpG4, CpG5, and CpG7 of SEQ ID NO: 4, at least CpG positions CpG7 of SEQ ID NO: 16, and at least CpG position CpG3 and CpG8 of SEQ ID NO: 20.

In some embodiments, the methods of the invention comprise a quantification of DNA methylation levels of at least CpG4 position of SEQ ID NO: 8, at least CpG position CpG7 of SEQ ID NO: 16, and at least CpG3 and CpG8 of SEQ ID NO: 20.

In some embodiments, the methods of the invention comprise a quantification of DNA methylation levels of at least CpG positions CpG1, CpG3, CpG4, CpG5, and CpG6 of SEQ ID NO: 12, at least CpG positions CpG7 of SEQ ID NO: 16, and at least CpG position CpG3 and CpG8 of SEQ ID NO: 20.

In preferred embodiments, the methods of the invention comprise a quantification of DNA methylation levels of CpG positions CpG2, CpG3, CpG4, CpG5, and CpG7 of SEQ ID NO: 4; CpG4 of SEQ ID NO: 8; CpG1, CpG3, CpG4, CpG5, and CpG6 of SEQ ID NO: 12; CpG7 of SEQ ID NO: 16; and CpG3 and CpG8 of SEQ ID NO: 20.

In further preferred embodiments, the methods of the invention comprise a quantification of DNA methylation levels of CpG positions CpG2, CpG3, CpG4, CpG5, and CpG7 of SEQ ID NO: 4; CpG4 of SEQ ID NO: 8; CpG1, CpG3, CpG4, CpG5, and CpG6 of SEQ ID NO: 12; and CpG3 and CpG8 of SEQ ID NO: 20.

In other preferred embodiments, the methods of the invention comprise a quantification of DNA methylation levels of CpG positions CpG2, CpG3, CpG4, CpG5, and CpG7 of SEQ ID NO: 4; CpG4 of SEQ ID NO: 8; CpG1, CpG3, CpG4, and CpG5 of SEQ ID NO: 12; and CpG3 and CpG8 of SEQ ID NO: 20.

In yet other preferred embodiments, the methods of the invention comprise a quantification of DNA methylation levels of CpG positions CpG2, CpG3, CpG4, and CpG7 of SEQ ID NO: 4; CpG4 of SEQ ID NO: 8; CpG1, CpG3, CpG4, and CpG5 of SEQ ID NO: 12; and CpG3 and CpG8 of SEQ ID NO: 20.

In some embodiments, the accuracy of an age determination according to the methods and materials of the invention is provided as a mean absolute error (MAE) between a chronological age of a subject and an estimated age obtained using the methods and materials of the invention.

For example, for an estimation of a predicted age according to methods and materials of the invention, a multivariate regression model was developed with the analysis of the experimental data obtained from a cohort of subjects. A leave-one-out analysis was performed, where the multivariate model was fit on all but one subject and its prediction could be related to the truly observed age of the left-out subject. This analysis was used as a validation technique to assess the predictive ability of the models according to the methods of the invention when tested in a dataset not used in the estimation.

For example, analysis according to the methods of the invention can be performed on fresh tissue, fresh-frozen tissue, conserved tissue by, e.g., formalin fixation and/or paraffin embedding, or unconserved partially decayed tissue.

The method according to the invention can be performed with any mammal having the above markers or orthologs or paralogs thereof. In preferred embodiments, the mammal is a mouse, rat, monkey or human. In most preferred embodiments, the mammal is a human.

Because in humans, age-related changes in DNA methylation status are tissue specific, the preferred tissue to be used in the methods of the invention is tooth tissue, more preferred, tooth pulp tissue. Other human tissue may also be used with the methods of the invention, e.g., tooth dentin, tooth cement, and bone tissue.

In some embodiments, methylation levels of specific CpG sites in specific genetic loci were quantified using pyrosequencing. The use of bisulfite DNA conversion followed by pyrosequencing permits the identification and quantification of methylation for clusters of CpG sites associated with a single epigenetic locus. Pyrosequencing permits the relative methylation at each CpG site to be measured at high accuracy. Further, pyrosequencing-based techniques utilize minimal DNA starting material permitting performance of other testing on limited quantities of sample including short tandem repeat analysis.

Advantageously, the methods and material of the instant invention allow age determination with only one or two PCR reactions for quick age estimation using pyrosequencing. The methods can further comprise bivariate analysis at each methylated site to identify CpG sites with the strongest correlation with age.

Further provided are methods for preparing a DNA sample for age determination of a subject. In some embodiments, the DNA sample for age determination comprises at least one amplicon of at least one gene selected from an ELOVL2, KLF14, SCGN, NPTX2, and/or FHL2 gene.

In specific embodiments, the DNA sample comprises at least one amplicon of at least two genes, at least three, or at least four genes of an ELOVL2, KLF14, SCGN, NPTX2, and/or FHL2 gene.

In some embodiments, the DNA sample comprises at least one amplicon of each of an ELOVL2, KLF14, SCGN, NPTX2, and an FHL2 gene.

In some embodiments, the DNA sample comprises an amplicon of at least an ELOVL2 gene and at least one further gene selected from a KLF14, SCGN, NPTX2, and/or FHL2 gene.

In some embodiments, if the DNA sample comprises an amplicon of an ELOVL2 gene it also comprises at least one amplicon of one gene from the group of an SCGN, KLF14, NPTX2, and/or FHL2 gene.

In some embodiments, the DNA sample comprises an amplicon of at least an ELOVL2 gene and at least an FHL2 gene.

In some embodiments, the DNA sample comprises an amplicon of at least an SCGN gene and at least one further gene selected from a KLF14, ELOVL2, NPTX2, and/or FHL2 gene.

In some embodiments, if the DNA sample comprises an amplicon a NPTX2 gene, it also comprises at least one amplicon of one gene from the group of an SCGN, KLF14, ELOVL2, and/or FHL2 gene.

In some embodiments, the DNA sample comprises an amplicon comprising SEQ ID NO: 4.

In some embodiments, the DNA sample comprises an amplicon comprising SEQ ID NO: 8.

In some embodiments, the DNA sample comprises an amplicon comprising SEQ ID NO: 12.

In some embodiments, the DNA sample comprises an amplicon comprising SEQ ID NO: 16.

In some embodiments, the DNA sample comprises an amplicon comprising SEQ ID NO: 20.

In some embodiments, the DNA sample comprises an amplicon comprising SEQ ID NO: 4 and at least one further amplicon comprising a sequence selected from SEQ ID NOs: 8, 12, 16, and 20.

In some embodiments, the DNA sample comprises an amplicon comprising SEQ ID NO: 8 and at least one further amplicon comprising a sequence selected from SEQ ID NOs: 12, 16, and 20.

In some embodiments, the DNA sample comprises an amplicon comprising SEQ ID NO: 12 and at least one further amplicon comprising a sequence selected from SEQ ID NOs: 16, and 20.

In some embodiments, the DNA sample comprises an amplicon comprising SEQ ID NO: 16 and at least one further amplicon comprising a sequence of SEQ ID NO: 20.

In some embodiments, the DNA sample comprises an amplicon each of SEQ ID NOs: 4, 8, 12, 16, and 20.

In some embodiments, the DNA sample comprises an amplicon each of SEQ ID NOs: 4, 8, 12, and 20.

In some embodiments, the DNA sample comprises one or more amplicons, each comprising a sequence selected from SEQ ID NOs: 4, 8, 12, 16, and 20.

In some embodiments, the method for preparing a DNA sample for age determination of a subject comprises the steps of:
  a) obtaining a tooth pulp tissue from the subject;
  b) isolating genomic DNA from the tooth tissue;
  c) bisulfite treating the genomic DNA;
  d) amplifying the bisulfite treated genomic DNA from step c) using at least one primer pair specific for an ELOVL2, FHL2, KLF14, SCGN, and/or a NPTX2 gene to generate the DNA sample;
  wherein the DNA sample comprises at least one amplicon from an ELOVL2, FHL2, KLF14, SCGN, and/or a NPTX2 gene; and
  wherein the number of CpGs and/or the number of TpGs present in the DNA sample determines the age of the subject.

In some embodiments, the method for preparing a DNA sample for age determination further comprises amplifying an amplicon of SEQ ID NO: 4 from an ELOVL2 gene.

In some embodiments, the method for preparing a DNA sample for age determination further comprises amplifying an amplicon of SEQ ID NO: 8 from a NPTX2 gene.

In some embodiments, the method for preparing a DNA sample for age determination further comprises amplifying an amplicon of SEQ ID NO: 12 from an FHL2 gene.

In some embodiments, the method for preparing a DNA sample for age determination further comprises amplifying an amplicon of SEQ ID NO: 16 from a KLF14 gene.

In some embodiments, the method for preparing a DNA sample for age determination further comprises amplifying an amplicon of SEQ ID NO: 20 from an SCGN gene.

Advantageously, in preferred embodiments, the DNA sample prepared according to the methods of the invention facilitates an age determination with an mean absolute error (MAE) between a chronological age of a subject and an estimated age obtained using the methods and materials of the invention of less than 2.5 years.

In some embodiments, the method for preparing a DNA sample for age determination is performed on a fresh tissue, fresh-frozen tissue, conserved tissue by, e.g., formalin fixation and/or paraffin embedding, or unconserved partially decayed tissue sample.

In some embodiments, the method of preparing a DNA sample is performed on a mammalian tissue sample; preferred a human tissue sample; more preferred a human tissue sample of a tooth and most preferred a human tissue sample of a tooth pulp.

In some embodiments, provided is a method for quantifying CpG methylation in a tooth sample derived from a subject, the method comprising analyzing the methylation status of at least one CpG position in a gene selected from ELOVL2, FHL2, KLF14, SCGN, and NPTX2, the method comprising:
  a) obtaining from the subject a tooth sample;
  b) isolating DNA from the tooth sample, preferably, tooth pulp sample;
  c) treating the DNA with bisulfite;
  d) amplifying the bisulfite treated DNA from step c) using a quantitative PCR system comprising a bisulfite specific primer pair that binds to a genetic locus selected from an ELOVL2, FHL2, KLF14, SCGN, and a NPTX2 gene;
  e) sequencing the amplified DNA of step d) using a sequencing primer that binds to a genetic locus selected from an ELOVL2, FHL2, KLF14, SCGN, and a NPTX2 gene; and
  f) quantifying the CpG and/or TpG dinucleotides present in the sequence of step e) wherein the number of CpG and/or TpG dinucleotides present in the sequence of step e) quantifies the CpG methylation in the tooth sample.

In one embodiment, the subject invention provides a method for age determination in a tooth sample derived from a subject based on the methylation status of at least one CpG position in a gene selected from ELOVL2, FHL2, KLF14, SCGN, and NPTX2, the method comprising:
  a) obtaining DNA from the tooth sample derived from the subject, preferably, tooth pulp sample;
  b) treating the DNA with bisulfite;
  c) amplifying the bisulfite treated DNA from using a quantitative PCR system comprising a bisulfite specific primer pair that binds to a genetic locus selected from an ELOVL2, FHL2, KLF14, SCGN, and a NPTX2 gene;
  d) sequencing the amplified DNA of step d) using a sequencing primer that binds to a genetic locus selected from an ELOVL2, FHL2, KLF14, SCGN, and a NPTX2 gene; and
  e) quantifying the CpG and/or TpG dinucleotides present in the sequence of step d), wherein the number of CpG and/or TpG dinucleotides present in the sequence of step d) determines the age of the subject.

In some embodiments, provided is a method for age determination in a tooth sample derived from a subject based on the methylation status of at least one CpG position in a gene selected from ELOVL2, FHL2, KLF14, SCGN, and NPTX2, the method comprising:
  a) obtaining from the subject a tooth sample;
  b) isolating DNA from the tooth sample, preferably, tooth pulp sample;
  c) treating the DNA with bisulfite;
  d) amplifying the bisulfite treated DNA from step c) using a quantitative PCR system comprising a bisulfite specific primer pair that binds to a genetic locus selected from an ELOVL2, FHL2, KLF14, SCGN, and a NPTX2 gene;
  e) sequencing the amplified DNA of step d) using a sequencing primer that binds to a genetic locus selected from an ELOVL2, FHL2, KLF14, SCGN, and a NPTX2 gene; and
  f) quantifying the CpG and/or TpG dinucleotides present in the sequence of step e), wherein the number of CpG and/or TpG dinucleotides present in the sequence of step e) determines the age of the subject.

In some embodiments, the amplifying step is performed using an adapter.

In one embodiment, the subject invention provides a method for age determination of a subject, the method comprising:
  a) obtaining a pulp tissue of a tooth of the subject;
  b) isolating genomic DNA from the pulp tissue;
  c) bisulfite treating the genomic DNA;
  d) amplifying the bisulfite treated genomic DNA from step c) to generate at least one DNA amplicon, which at least one DNA amplicon comprises a continuous DNA sequence from an ELOVL2, NPTX2, FHL2, KLF14, and/or an SCGN gene, wherein the continuous DNA sequence comprises at least one dinucleotide selected from a CpG and a TpG;
  e) sequencing the at least one DNA amplicon from step d) with at least one sequencing primer that is complementary to the at least one DNA amplicon;

f) quantifying the CpG, if any, and/or the TpG, if any, of the at least one dinucleotide of the continuous DNA sequence; and g) determining the age of the subject from the quantity of CpG, if any, compared to the quantity of TpG, if any of the at least one dinucleotide.

In one embodiment, the continuous DNA sequence of the at least one amplicon comprises at least 2, 3, 4, 5, 6, 7, 8, 9, 10, 11, 12, 13, 14, 15, 16, 17, 18, 19, or 20 dinucleotides selected from CpG and TpG. Preferably, the continuous DNA sequence of the at least one amplicon comprises between two and fifteen dinucleotides each selected from CpG and TpG.

In one embodiment, step d) of the method for age determination comprises amplifying the bisulfite treated genomic DNA from step c) to generate at least two DNA amplicons, which at least two DNA amplicons comprise a continuous DNA sequence from an ELOVL2, NPTX2, FHL2, KLF14, and/or an SCGN gene.

Advantageously, the methods of the invention are fast and low cost because they obviate large scale genome sequencing while providing advantageous age prediction accuracy based on a small number of data points.

In some embodiments, simple linear regression models are provided to measure age-correlation values. Advantageously, in preferred embodiments, the simple linear age prediction models based on the specific genes of the invention provide mean absolute deviation (MAD) values from chronological age below 2.5 years.

In some embodiments, the accuracy of the models of the invention is validated using fold and leave-one-out cross-validation. In the fold cross-validation technique, a dataset is randomly split into subsets, folds, of the same size. Each fold is then used once as a testing or validation set while the remaining folds are used as training sets. The errors of each round are averaged to obtain a mean absolute error, which is computed as the mean of the absolute derivations between an observed age and predicted age.

In some embodiments, leave-one-out cross validation is used where one observation is left out of each round and age is predicted given all the other observations.

In some embodiments, a variation inflation factor (VIF) is used to measure the inflation of the variance of an estimated regression coefficient due to the presence of correlated predictors to detect collinearity among predictor variables in the models. For example, when the VIF value is higher than 5, multicollinearity is suspected.

In some embodiments, the methods and materials of the invention provide an accuracy in age determination in the range from a low of about 1 year to a high of about 6 years; or about 1.2 years to about 5.8 years; about 1.3 years to about 5.6 years; about 1.4 years to about 5.4 years; about 1.5 years to about 5.2 years; about 1.6 years to about 5 years; about 1.7 years to about 4.8 years; about 1.8 years to about 4.6 years; about 1.9 years to about 4.4 years; about 2 years to about 4.2 years; about 2.1 years to about 4 years; about 2.2 years to about 3.8 years; about 2.3 years to about 3.6 years; about 2.4 years to about 3.4 years; about 2.5 years to about 3.2 years; about 2.6 years to about 3 years; about 2.7 years to about 2.8 years; or about 1 year, 1.2 years, 1.3 years, 1.4 years, 1.5 year, 1.6 years, 1.7 years, 1.8 years, 1.9 years, 2 years, 2.1 years, 2.2 years, year, 2.3 years, 2.4 years, 2.5 years; 2.6 years, 2.7 years, 2.8 years, 2.9 years, 3 years, 3.1 years, 3.2 years, 3.3 years, 3.4 years, 3.5 years, 3.6 years, 3.7 years, 3.8 years, 3.9 years or 4 years. In preferred embodiments, the methods and materials of the invention provide an accuracy of age determination between 1.2 years and 2.5 years.

In more preferred embodiments, the methods and materials of the invention provide an accuracy of age determination between 1.4 years and 2.2 years. In most preferred embodiments, the methods and materials of the invention provide an accuracy of age determination between 1.5 years and 2.1 years.

Advantageously, the methods described herein can be practiced with minute amounts of genomic DNA, for example, between 1 ng to 50 ng, particularly, between 5 ng to 30 ng, more particularly, at about 20 ng.

In one embodiment, the subject invention further provides a kit for age determination of a sample, the kit comprising one or more of the following:

1) one or more extraction reagents for isolating the genomic DNA from the sample;

2) one or more bisulfite treatment reagents for bisulfite treating the genomic DNA;

3) one or more amplification reagents for amplifying the bisulfite treated genomic DNA, including one or more primer pairs of SEQ ID NOs: 1 and 2, 5 and 6, 9 and 10, 13 and 14, and/or 17 and 18;

4) one or more sequencing reagents, including one or more sequencing primer selected from SEQ ID NOs: 3, 7, 11, 15, and 19;

5) tools for obtaining the sample; and 6) instructions for using the kit.

In one embodiment, the subject invention further provides a kit for preparing a DNA sample for age determination, the kit comprising one or more of the following:

1) one or more extraction reagents for isolating the genomic DNA from the sample;

2) one or more bisulfite treatment reagents for bisulfite treating the genomic DNA;

3) one or more amplification reagents for amplifying the bisulfite treated genomic DNA, including one or more primer pairs of SEQ ID NOs: 1 and 2, 5 and 6, 9 and 10, 13 and 14, and/or 17 and 18;

4) one or more sequencing reagents, including one or more sequencing primer selected from SEQ ID NOs: 3, 7, 11, 15, and 19; and 5) instructions for using the kit.

In a specific embodiment, the kit of the subject invention comprises one or more of:

i) primer pair of SEQ ID NOs: 1 and 2, and/or SEQ ID NO: 3;

ii) primer pair of SEQ ID NOs: 5 and 6, and/or SEQ ID NO: 7;

iii) primer pair of SEQ ID NOs: 9 and 10, and/or SEQ ID NO: 11;

iv) primer pair of SEQ ID NOs: 13 and 14, and/or SEQ ID NO: 15; and v) primer pair of SEQ ID NOs: 17 and 18, and/or SEQ ID NO: 19.

Definitions

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting essentially of" or "consists essentially of" indicate that the claim encompasses embodiments containing the specified materials or steps and those that do not materially affect the basic and novel characteristic(s) of the claim. Use of the term "comprising" contemplates other embodiments that "consist of" or "consisting essentially of" the recited component(s).

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

As used herein, the term "level of methylation" or "methylation status" as applied to a genetic locus refers to whether one or more cytosine residues present in a CpG have or do not have a methylation group. The level of methylation or methylation status refers to the percentage of cells in a sample that do or do not have a methylation group on such cytosines. For example, if 50 cells in a pool of 100 cells contain methylated cytosines at a CpG site, the level of methylation or methylation status of the CpG site is 50%.

Various techniques are known to a person of ordinary skill in the art to determine the level of methylation at the specific loci in a genomic DNA. Non-limiting examples of such techniques include bisulfite conversion, HRM, digestion by restriction enzymes followed by PCR, Combined Bisulfite Restriction Analysis (COBRA), direct sequencing, cloning and sequencing, bisulfite treatment and sequences, bisulfite treatment and pyrosequencing, mass spectrometry analysis or probe/microarray based assay. Certain techniques of determining methylation at certain genomic sites are described in Eads et al., Xiong et al., Paul et al., Warnecke et al., Tost et al., and Ehrich et al., the contents of which are herein incorporated in their entirety. Additional techniques for determining the level of methylation at a genetic are known to a person of ordinary skill in the art and such techniques are within the purview of the invention.

An "adapter" as used herein is a sequence of about 10 to 20 nucleotides that can be introduced into an amplicon by incorporating the adapter into the primer used for the amplification of the amplicon. Once an amplicon contains an adapter sequence, a primer designed based on the sequence of the amplicon can be used to sequence the amplicon.

A primer pair is a pair of oligonucleotides, each having about 15 to 25 nucleotides, and designed to amplify a specific locus from template DNA. Guidelines for designing a primer pair to amplify a specific locus to in a template DNA are well known in the art.

A singleplex PCR is a reaction where only one set of primers is used per reaction; whereas a multiplex reaction is one that uses multiple primer sets per PCR reaction.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The present invention is further illustrated by the following examples that should not be construed as limiting. The contents of all references, patents, and published patent applications cited throughout this application, as well as the FIGURES, are incorporated herein by reference in their entirety for all purposes.

Material and Methods

Sample Collection and Teeth Processing

Twenty healthy erupted third molars were collected from patients in a dental clinic in Spain (age range: 22-70 years old). All dental elements originated from different individuals. Sample data were limited to sex, age, and population group. Teeth were washed with a soft toothbrush under running sterile distilled water and dried at room temperature. Teeth were irradiated for 15 minutes per side with ultraviolet light (254 nm) to eliminate exogenous DNA. Enamel and cementum were removed using a diamond brush. In the midline between cementum and enamel, crowns were separated from the roots using a diamond-cutting disc. The roots were cut along the midline and the pulp was removed using a spoon excavator.

DNA Extraction

DNA was extracted from pulp using DNeasy Blood and Tissue Kit (Qiagen, GmbH, Germany), according to the manufacturer's protocol. DNA was eluted in 35 µl Buffer AE.

DNA Quantification

DNA was quantified using Qubit dsDNA HS Assay Kit (Thermo Fisher Scientific, Waltham, Mass.), according to the manufacturer's protocol.

Bisulfite Conversion and PCR 200 ng of DNA was bisulfite converted using the EpiTect Fast Bisulfite Conversion Kit (Qiagen, GmbH, Germany). Converted DNA was eluted with 20 µl of elution buffer. 1.5 µl of converted DNA was amplified by singleplex PCR in a total volume of 0.2 µM of primers for KLF14, NPTX2, ELOVL2, FHL2, SCGN and 2× Qiagen PyroMark PCR Master Mix (Qiagen, GmbH, Germany). All primer sequences are listed in table 1. PCR reactions consisted of initial hold at 95° C. for 15 min followed by 45 cycles of 30 s at 94° C., 30 s at 56° C., 30 s at 72° C. PCR amplification ended with a final extension step at 72° C. for 10 min.

TABLE 1

Primer sequences to evaluate CpG sites in five different genes. *biotinylated primer. Y-location of CpGs (pyrimidine C or T); R-location of CpGs (purine A or G).

| Gene | Primer | Sequence | CpG sites analyzed (in bold) |
|---|---|---|---|
| ELOVL2 | Forward* | AGGGGAGTAGGGT AAGTGAGG (SEQ ID NO: 1) | CCRTAAACRTTAAACCRCCRC RCRAAACCRAC (SEQ ID NO: 4) |
| | Reverse | AACAAAACCATTT CCCCCTAATAT (SEQ ID NO: 2) | |
| | Sequencing | ACAACCAATAAAT ATTCCTAAAACT (SEQ ID NO: 3) | |
| NPTX2 | Forward | GGTTGTGAGAAGG TAGGAGATTT (SEQ ID NO: 5) | TYGYGGTGTAYGYGATTTTYG AGAYGATAGYGYGGTTATTGT TAGTAGYGAAGGYGTTTTTYG YGGAGYGTTTYGA (SEQ ID NO: 8) |
| | Reverse* | ACCAACAACCCCA ACATCCC (SEQ ID NO: 6) | |
| | Sequencing | AGAAGGTAGGAG ATTTTTGTT (SEQ ID NO: 7) | |
| FHL2 | Forward | TGTTTTTAGGGTTT TGGGAGTATAG (SEQ ID NO: 9) | AGTTATYGGGAGYGTYGTTTTY GGYGTGGGTTTTYGGGYGAGT TTYGG (SEQ ID NO: 12) |
| | Reverse* | ACACCTCCTAAAA CTTCTCCAATCTCC (SEQ ID NO: 10) | |
| | Sequencing | GGTTTTGGGAGTA TAGT (SEQ ID NO: 11) | |
| KLF14 | Forward | TTTGGTGTAGTTA GGGAAGGGGTATT (SEQ ID NO: 13) | TGGYGTTTGGTAGTAGGTGTGA TAGATTTTTTTYGGGGYGTTTG ATTYGYGGYGGGGGYGGGGTT TGTTTTTAGGGTTTTTTTAG (SEQ ID NO: 16) |
| | Reverse* | CACCAACAACCTC TAATAAATTCTCT A (SEQ ID NO: 14) | |
| | Sequencing | GGGAAGGGGTATT GG (SEQ ID NO: 15) | |
| SCGN | Forward | AAGGAGTTTTTTTT AAAGTTGTTTAGG (SEQ ID NO: 17) | TTYGYGTYGGTGTTTGGTTTTY GTYGTTAATATTATGGATAGTT TTYGGGAATYGATTTTGGGGY GTTTGGAYGTYGTTGGTTTTTG GTAG (SEQ ID NO: 20) |
| | Reverse* | ACAACCCAAATCC ATAACTTTTCCTAC A (SEQ ID NO: 18) | |
| | Sequencing | TTTTTTTAAAGTTG TTTAGGTTTT (SEQ ID NO: 19) | |

Pyrosequencing

Methylation levels were assessed after loading 15 µl of PCR product into the PyroMark Q48 Instrument (Qiagen, GmbH, Germany), and performed pyrosequencing with 0.4 µM of sequencing primers following manufacturer's instructions.

Methylation Results Analyses and Statistics

Pyrosequencing results were analyzed using the PyroMark Q48 Autoprep software (Qiagen, GmbH, Germany). Statistical analyses were performed using IBM SPSS 26 (IBM, Armonk, N.Y.). Firstly, simple correlation analyses were performed between age and methylation levels of KLF14, NPTX2, ELOVL2, FHL2, and SCGN CpGs. Unexpectedly high correlation values for methylation at the five genetic loci were obtained. After detailed analysis of DNA methylation at single CpGs, a multiple linear regression model was used to predict age from DNA methylation data. To this end, beta values were calculated by considering methylation values and chronological age of each subject in a test group according to the following formula:

$$\text{Age} = b_0 + b_1 \text{CpG}_1 + b_2 \text{CPG}_2 + \ldots + b_N \text{CpG}_N$$

The estimated age of the individual was calculated by plugging the beta values and the methylation values of the selected CpGs into this formula. For pulp, a multiple linear regression model was then calculated by considering for each gene only the CpGs that turned out to be strongly correlated with age. Further, a multiple linear regression model is calculated by grouping DNA methylation values that best correlate with age and calculate the median of the absolute difference between actual individual age and the age calculated by considering DNA methylation levels (methAge).

Multivariate linear regression models were performed to predict age. Validation of the models was performed by Leave-one-out cross validation (LOOCV), in which one observation is left out and used as validation set and the remaining samples as training set. This was repeated 20 times so that a complete LOOCV was performed.

Example 1—Methods/Calculations

DNA methylation is one of the epigenetic mechanisms for gene regulation. Different levels of DNA methylation in certain loci control gene expression by silencing or activating specific genes. Some loci on the genome called "tissue-specific differentially methylated regions" (tDMRs) can, therefore, be used for cell identification because they present different levels of DNA methylation depending on the cell studied.

To determine the pattern of DNA methylation at a locus, the most commonly used methods include the bisulfite modification of genomic DNA, which chemically converts the unmethylated cytosines to uracils but does not react with methylated cytosines. During a polymerase chain reaction (PCR) the uracils get copied as thymines and the amplicons can then be sequenced to determine the presence of a cytosine or a thymine at each specific CpG.

For each locus, the percent methylation values were obtained at each CpG site. Linear regression analysis was used to calculate a correlation between age and DNA methylation. A single regression analysis was performed to examine each CpG site one at a time. Next, a simultaneous analysis of all tested cytosines was performed using multivariate linear regression.

Example 2—CpG Sites Identified and Individual Correlations with Age

46 CpGs sites located at ELOVL2, KLF14, SCGN, NPTX2, and FHL2 were identified and their methylation levels were assessed through pyrosequencing. Correlation coefficients of these CpGs sites with age were calculated (Table 2). Positive and significant correlations were found in six ELOVL2 CpGs sites with r between 0.308-0.365 except for CpG5, which produced an r=0.240 and was not significant. In contrast to these results, among seven CpGs evaluated on KLF14, only one, CpG7 showed a positive and significant correlation with age (r=0.468). The same thing happened with NPTX2, as only CpG4 showed a significant and positive correlation with age (r=0.327). Correlations of methylation levels of CpGs located in FHL2 and age were negative, however, while CpG1 and CpG2 showed a high correlation (r=0.367 and r=0.376, respectively), the results were not significant.

TABLE 2

Correlation coefficients and significance of CpG sites identified in ELOVL2, KLF14, SCGN, NPTX2, and FHL2

| Gene | Site | r | p-value |
|---|---|---|---|
| ELOVL2 | CpG1 | 0.353 | 0.024 |
|  | CpG2 | 0.308 | 0.043 |
|  | CpG3 | 0.341 | 0.028 |
|  | CpG4 | 0.318 | 0.038 |
|  | CpG5 | 0.240 | 0.093 |
|  | CpG6 | 0.342 | 0.028 |
|  | CpG7 | 0.365 | 0.020 |
| KLF14 | CpG1 | 0.168 | 0.480 |
|  | CpG2 | 0.316 | 0.174 |
|  | CpG3 | 0.154 | 0.518 |
|  | CpG4 | 0.278 | 0.236 |
|  | CpG5 | 0.267 | 0.256 |
|  | CpG6 | 0.220 | 0.350 |
|  | CpG7 | 0.468 | 0.037 |
| SCGN | CpG1 | 0.313 | 0.180 |
|  | CpG2 | 0.344 | 0.138 |
|  | CpG3 | 0.529 | 0.017 |
|  | CpG4 | 0.340 | 0.142 |
|  | CpG5 | −0.103 | 0.665 |
|  | CpG6 | 0.268 | 0.254 |
|  | CpG7 | 0.258 | 0.272 |
|  | CpG8 | 0.508 | 0.022 |
|  | CpG9 | 0.156 | 0.512 |
|  | CpG10 | 0.291 | 0.213 |
| NPTX2 | CpG1 | 0.280 | 0.076 |
|  | CpG2 | −0.105 | 0.514 |
|  | CpG3 | −0.084 | 0.601 |
|  | CpG4 | 0.327 | 0.037 |
|  | CpG5 | 0.214 | 0.179 |
|  | CpG6 | 0.022 | 0.890 |
|  | CpG7 | 0.121 | 0.449 |
|  | CpG8 | 0.151 | 0.346 |
|  | CpG9 | 0.076 | 0.637 |
|  | CpG10 | 0.136 | 0.396 |
|  | CpG11 | 0.172 | 0.282 |
|  | CpG12 | 0.127 | 0.428 |
|  | CpG13 | 0.166 | 0.300 |
|  | CpG14 | 0.136 | 0.556 |
| FHL2 | CpG1 | −0.367 | 0.111 |
|  | CpG2 | −0.376 | 0.094 |
|  | CpG3 | −0.251 | 0.285 |
|  | CpG4 | −0.288 | 0.217 |
|  | CpG5 | −0.262 | 0.264 |
|  | CpG6 | −0.241 | 0.305 |
|  | CpG7 | −0.088 | 0.713 |
|  | CpG8 | −0.086 | 0.720 |

Example 3—Construction of Prediction Models for Age Estimation

A backward stepwise multiple linear regression analysis was performed to create prediction models for age estimation based on these five genes and their CpGs producing r>0.20, and selected after assessment on each gene of individual and significant CpG contribution to age. These models are shown in Table 3. The model with the highest correlation coefficient ($R^2$=0.975) and Mean Absolute Error (MAE) between chronological and estimated age of 1.5474 included the majority of the ELOVL2, NPTX2, KLF4, SCGN significant CpGs, and also, some CpGs from FHL2. Although individually FHL2 did not retrieve significant correlations, it appeared to play a role in age estimation when combined with other markers.

The second model removed KLF14 CpG7, obtaining a significant and strong correlation coefficient ($R^2$=0.972) and MAE between chronological and estimated age of 1.711. The next model eliminated FHL2 CpG6, obtaining high correlation coefficient $R^2$=0.961, and MAE between chronological and estimated age 2.047. The last model removed ELOVL2 CpG5, (p=0.0001), producing an $R^2$=0.955, and MAE 2.1313.

TABLE 3

Prediction models for age estimation in pulp.
MAE, Mean Absolute Error; LOOCV, Leave-one-out cross-validation.

| Model | R | $R^2$ | SE | p-value | MAE | MAE (LOOCV) |
|---|---|---|---|---|---|---|
| Age (years) = 12.763 + 4.034(ELOVL2CpG3) + 3.535(ELOVL2CpG4) − 3.040(ELOVL2CpG7) + 7.815(NPTX2CpG4) + 3.791(SCGNCpG3) + 9.122(SCGNCpG8) − 5.013(ELOVL2CpG2) − 1.643(ELOVL2CpG5) − 4.341(FHL2CpG1) + 3.571(FHL2CpG3) − 1.093(FHL2CpG4) + 3.882(FHL2CpG5) − 1.229(FHL2CpG6) − 1.662(KLF14CpG7) | 0.987 | 0.975 | 3.671 | 0.004 | 1.5474 | 2.128 |
| Age (years) = 14.710 + 3.675(ELOVL2CpG3) − 3.972(ELOVL2CpG4) + 2.978(ELOVL2CpG7) + 5.278(NPTX2CpG4) + 4.044(SCGNCpG3) − 8.378(SCGNCpG8) − 4.853(ELOVL2CpG2) − 1.875(ELOVL2CpG5) − 4.273(FHL2CpG1) + 3.547(FHL2CpG3) − 1.145(FHL2CpG4) + 3.640(FHL2CpG5) − 0.937(FHL2CpG6) | 0.986 | 0.972 | 3.505 | 0.001 | 1.711 | 1.706 |
| Age (years) = 14.349 + 4.635(ELOVL2CpG3) − 3.049(ELOVL2CpG4) + 3.681(ELOVL2CpG7) + 5.254(NPTX2CpG4) + 3.810(SCGNCpG3) − 9.503(SCGNCpG8) − 4.835(ELOVL2CpG2) − 0.982(ELOVL2CpG5) − 4.191(FHL2CpG1) + 3.778(FHL2CpG3) − 1.447(FHL2CpG4) + 2.638(FHL2CpG5) | 0.980 | 0.961 | 3.874 | 0.001 | 2.047 | 2.083 |
| Age (years) = 14.854 + 5.139(ELOVL2CpG3) + 2.249(ELOVL2CpG4) − 4.086(ELOVL2CpG7) + 6.927(NPTX2CpG4) + 3.505(SCGNCpG3) + 10.363(SCGNCpG8) − 4.983(ELOVL2CpG2) − 4.223(FHL2CpG1) + 4.075(FHL2CpG3) − 1.562(FHL2CpG4) + 2.506(FHL2CpG5) | 0.977 | 0.955 | 3.866 | 0.0001 | 2.1313 | 1.942 |

Example 4—Evaluation of the Models

Due to the size of the sample, leave-one-out cross-validation was chosen to validate the models. Using this procedure, Model 1 showed the highest estimation error, followed by Model 4. Cross-validation of Models 2 and 4 produced the best accuracy.

Figure 1B:
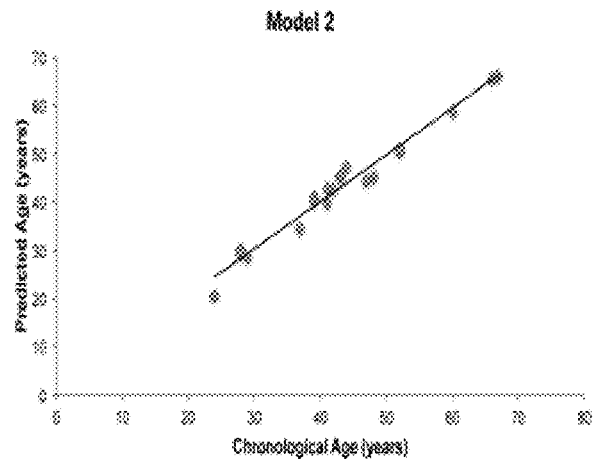
FIG. 1B shows the predicted versus chronological age determining by model 2.
Figure 1C:
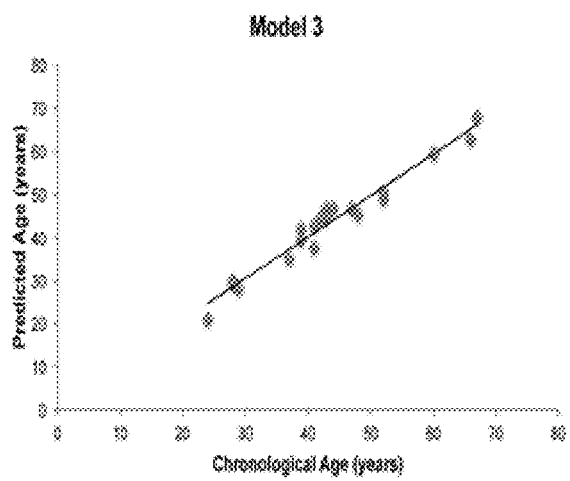
FIG. 1C shows the predicted versus chronological age determining by model 3.
Figure 1D:
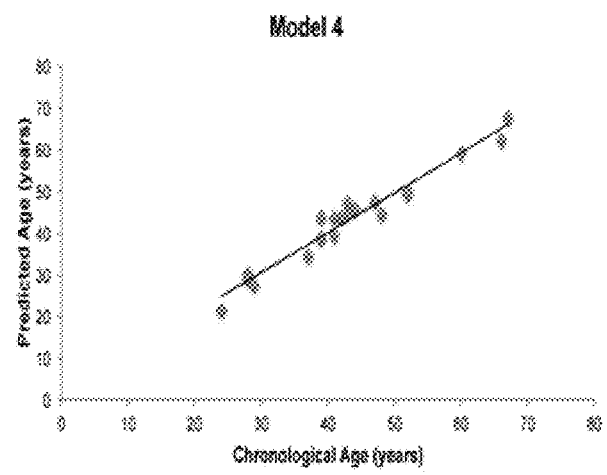
FIG. 1D shows the predicted versus chronological age determining by model 4.

Additionally, Pearson correlations were carried out to compare the predictive ages and chronological ages, resulting in nearly the same correlation in the first three models (r=0.98) and a slightly lower correlation in the fourth model (r=0.97). These correlations between predictive and chronological ages are depicted in FIG. 1.

Example 5—Determination of Age-at-Death Estimates

In this study the DNA methylation levels of five genes (ELOVL2, NPTX2, KLF14, SCGN, and FHL2) and their correlation with the age in pulp tissue from adult individuals were evaluated in order to improve age-at-death estimates in forensic anthropology. Pulp was chosen, as it is the inner layer of the teeth, well protected from external insults. The results showed that a multivariate model, based on DNA methylation levels of certain CpGs of these genes was required to accurately determine the age with MAE between 1.5-2.13 years.

In the instant experiments, three dental layers, cementum, dentin and pulp were tested and multivariate models were used, which models provided the most accurate age estimate and obtained the best correlation with pulp (difference between chronological and predicted age 2.25 years), and the worst with dentin (difference between chronological and predicted age 7.07 years).

Advantageously, the combination of cementum and pulp analyses retrieved the best estimation (difference between chronological and predicted age 1.20 years). These results demonstrate a surprising improvement on age estimates in pulp. Additionally, the results demonstrated that the type of tooth and sex did not have an impact on the estimates.

FHL2, is a transcriptional co-factor involved in different process: cell cycle regulation, bone formation, and wound healing.

KLF14 is a member of the Krüppel-like factor family of transcription factors, regulating among others, gene expression in adipose tissues.

In the present study, SCGN seemed to play a key role in age estimation, as both CpGs 3 and 8 were kept in the four models and produced among the highest correlations in the genes analyzed (except ELOVL2 CpG1 and CpG7). NPTX2 (neuronal pentraxin II) is involved in synapse formation, as pulp also contains nerve cells, the methylation levels of this gene also show a response with age. Only one CpG, CpG4 was kept through the four models.

The present study validated the usefulness of ELOVL2 and FHL2 as targets for age estimation in dental tissues, and also, identified new potential markers: KLF14, SCGN, and NPTX2.

Example 5—Sanger Sequencing

After bisulfite conversion, the modified DNA samples were submitted to PCR for selected regions of genes ELOVL2, FHL2, NPTX2, KLF14, and SCGN using the Qiagen Multiplex PCR kit (Qiagen, Hilden, Germany) and sequenced with Big-Dye Terminator v1.1 Cycle Sequencing kit (Applied Biosystems).

Example 6—Snapshot Assay

After bisulfite conversion, the modified DNA samples were submitted to a multiplex SNaPshot assay for 5 CpG sites at genes ELOVL2, FHL2, NPTX2, KLF14, and SCGN. Multiplex PCR amplification and multiplex SBE (single-base extension) reactions were performed.

All patents, patent applications, provisional applications, and publications referred to or cited herein are incorporated by reference in their entirety, including all FIGURES and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method for age determination of a subject comprising
   a) obtaining a pulp tissue of a tooth of the subject;
   b) isolating genomic DNA from the pulp tissue;
   c) bisulfite treating the genomic DNA;
   d) amplifying the bisulfite treated genomic DNA from step c) to generate at least two DNA amplicons from at least two genes selected from ELOVL2, NPTX2, FHL2, KLF14, and SCGN genes;
   e) sequencing the at least two DNA amplicons from step d) with at least two sequencing primers that are complementary to the at least two DNA amplicons;
   f) quantifying at least one dinucleotide selected from CpG, if any, and TpG, if any, of the at least two DNA amplicons; and
   g) determining the age of the subject from the quantity of CpG, if any compared to the quantity of TpG, if any, of the at least one dinucleotide.

2. The method according to claim 1, the at least two amplicons each comprising at least two dinucleotides selected from CpG and TpG.

3. The method according to claim 1, the at least two amplicons each comprising between two and fifteen dinucleotides each selected from CpG and TpG.

4. The method according to claim 1, step d) comprising amplifying the bisulfite treated genomic DNA from step c) to generate at least three DNA amplicons from at least three genes selected from ELOVL2, NPTX2, FHL2, KLF14, and SCGN genes.

5. The method according to claim 1, the at least two DNA amplicons being selected from sequences comprising at least one of SEQ ID NOs: 4, 8, 12, 16 and 20.

6. The method according to claim 5, the amplifying step d) comprising using at least two primer pairs selected from SEQ ID NOs: 1 and 2, 5 and 6, 9 and 10, 13 and 14, and 17 and 18.

7. The method according to claim 6, the sequencing step e) comprising using at least two primers of SEQ ID NOs: 3, 7, 11, 15, and 19.

8. The method according to claim 1, the sequencing step being performed using pyrosequencing.

9. The method according to claim 1, the determining step g) comprising:
   i) selecting at least four genes from the group consisting of an ELOVL2, NPTX2, FHL2, KLF14, and an SCGN gene; and
   ii) performing a multivariant analysis on the selected at least four genes.

10. The method according to claim 9, the selected at least four genes comprising an ELOVL2 gene.

11. The method according to claim 9, the multivariant analysis providing an accuracy of age determination of 2.5 years or less.

12. A method for preparing a DNA sample for age determination of a subject, the method comprising the steps of:
   a) obtaining a tooth tissue from the subject;
   b) isolating genomic DNA from the tooth tissue;

c) bisulfite treating the genomic DNA;
d) amplifying the bisulfite treated genomic DNA from step c) using at least one primer pair specific for an ELOVL2, FHL2, KLF14, SCGN, and/or an NPTX2 gene to generate the DNA sample, the at least one primer pair being selected from SEQ ID NOs: 1 and 2, 5 and 6, 9 and 10, 13 and 14, and 17 and 18;

the DNA sample comprising at least one amplicon from an ELOVL2, FHL2, KLF14, SCGN, and/or an NPTX2 gene; and the at least one amplicon comprising a number of CpGs and/or a number of TpGs, which determines the age of the subject.

13. The method according to claim 12, the DNA sample comprising at least two amplicons from an ELOVL2, FHL2, KLF14, SCGN, and/or an NPTX2 gene.

14. The method according to claim 12, the DNA sample comprising at least one amplicon from an FHL2, KLF14, SCGN, and/or an NPTX2 gene if it does comprise an amplicon from an ELOVL2 gene.

15. The method according to claim 12, the DNA sample comprising at least one amplicon from an SCGN gene.

16. The method according to claim 12, the DNA sample comprising at least one amplicon from an NPTX2 gene.

17. The method according to claim 12, the DNA sample comprising at least two amplicons from an ELOVL2, FHL2, KLF14, SCGN, and/or NPTX2 gene.

18. The method according to claim 12, the DNA sample comprising at least three amplicons from an ELOVL2, FHL2, KLF14, SCGN, and/or NPTX2 gene.

19. The method according to claim 12, the DNA sample comprising at least four amplicons from an ELOVL2, FHL2, KLF14, SCGN, and/or NPTX2 gene.

20. A kit comprising:
   i) primer pair of SEQ ID NOs: 1 and 2, and/or SEQ ID NO: 3;
   ii) primer pair of SEQ ID NOs: 5 and 6, and/or SEQ ID NO: 7;
   iii) primer pair of SEQ ID NOs: 9 and 10, and/or SEQ ID NO: 11;
   iv) primer pair of SEQ ID NOs: 13 and 14, and/or SEQ ID NO: 15; and
   v) primer pair of SEQ ID NOs: 17 and 18, and/or SEQ ID NO: 19.

* * * * *